United States Patent [19]

Outtrup et al.

[11] Patent Number: 5,466,594
[45] Date of Patent: Nov. 14, 1995

[54] **ALKALINE PROTEASE *BACILLUS SP.* JP 395, METHOD OF MAKING AND DETERGENT COMPOSITIONS**

[75] Inventors: Helle Outtrup, Ballerup; Claus Dambmann, Soeborg; Margrethe Christiansen, Klampenborg; Dorrit A. Aaslyng, Roskilde, all of Denmark

[73] Assignee: Novo Nordisk A/S, Bagsvaerd, Denmark

[21] Appl. No.: 119,193

[22] PCT Filed: Apr. 3, 1992

[86] PCT No.: PCT/DK92/00105

§ 371 Date: Sep. 23, 1993

§ 102(e) Date: Sep. 23, 1993

[87] PCT Pub. No.: WO92/17578

PCT Pub. Date: Oct. 15, 1992

[30] Foreign Application Priority Data

Apr. 3, 1991 [DK] Denmark .................. 0585/91

[51] Int. Cl.$^6$ .................. C12N 9/52; C12N 9/54; C12N 1/70; C11D 9/40
[52] U.S. Cl. .................. 435/221; 435/220; 435/252.31; 435/832; 252/174.12
[58] Field of Search .................. 435/220, 221, 435/252.31, 832; 252/174.12

[56] References Cited

U.S. PATENT DOCUMENTS 5,288,627  2/1994  Nielsen et al. .................. 435/223
5,296,367  3/1994  Hitomi et al. .................. 435/221

FOREIGN PATENT DOCUMENTS 0204342  12/1986  European Pat. Off. .
1101884  4/1989  Japan .
2255087  10/1990  Japan .

OTHER PUBLICATIONS

Stepanov et al., (1977) *Acta, Biol, Med. Germ.*, 36, 1509–1514.
P. Gemeiner et al., *Folia Microbiol.*, vol. 36, No. 3, pp. 283–293, 1991.
H. Horikoshi, *Agr. Biol. Chem.*, vol. 35, No. 9, pp. 1407–1414, 1971.
Y. Takii et al., *Appl. Microbiol. Biotechnol.*, vol. 34, pp. 57–62, 1990.

*Primary Examiner*—Marian C. Knode
*Assistant Examiner*—Jon P. Weber
*Attorney, Agent, or Firm*—Steve T. Zelson; Elias J. Lambiris

[57] ABSTRACT

An alkaline protease from a strain of Bacillus sp. JP 395 has been isolated. The protease has a mass of about 30 kDa as determined by SDS-PAGE, a pH optimum of about 9–11, a temperature optimum of about 50°–65° C., and an isoelectric point above 9.5. The protease is inhibited by PMSF (phenylmethylsulfonylfluoride), but not by EDTA or soybean protein inhibitor. The protease is prepared by growing this strain of bacillus in a suitable media and recovering the protease. The protease has been formulated in detergents and is stable at 40° C. for 60 minutes in these detergents under wash conditions in the presence or absence of bleaches such as perborate.

10 Claims, 1 Drawing Sheet

ALKALINE PROTEASE BACILLUS SP. JP 395, METHOD OF MAKING AND DETERGENT COMPOSITIONS

CROSS-REFERENCE TO RELATED APPLICATIONS

This application is a continuation of PCT/DK92/00105 filed Apr. 3, 1992, which is incorporated herein by reference.

TECHNICAL FIELD

This invention is in the field of detergent proteases derived from strains of alkalophilic Bacillus sp. More specifically, the invention is directed towards a novel alkaline protease derived from a strain of Bacillus sp. JP 395. Moreover, the invention is directed towards a process for the preparation of the protease, the use of the protease as detergent enzyme, and detergent compositions comprising the protease of the invention.

BACKGROUND ART

Detergent enzymes have been marketed for more than 20 years and are now well established as normal detergent ingredients in both powder and liquid detergents all over the world. With the trend towards lower temperature washing, detergent enzyme consumption has increased during late years. Enzymes used in washing formulations comprise proteases, lipases, amylases, cellulases, as well as other enzymes, or mixtures hereof. Commercially most important are proteases.

Detergent proteases have been developed by isolation of proteases found in nature followed by testing in detergent formulations. Most detergent proteases are obtained from members of the genus Bacillus. Currently new types of proteases enter the market, offering the possibility of giving a better cost/performance ratio at various specified conditions.

Examples of commercial protease products are ALCALASE™, ESPERASE™ and SAVINASE™, all supplied by Novo Nordisk A/S, Denmark. These and similar enzyme products from other commercial sources are active in detergent solutions, i.e. at pH values in the range of from 8 to 11 and in the presence of sequestering agents, surfactants and bleaching agents such as sodium borate. The ALCALASE™ protease is produced by strains of the species *Bacillus ficheniformis*. The ESPERASE™ and SAVINASE™ proteases are obtained by cultivation of strains of alkalophilic Bacilli.

SUMMARY OF THE INVENTION

According to the present invention novel detergent proteases are provided.

In its first aspect, the invention provides a protease having an apparent molecular weight of 30 kD, a pI above 9.5, pH optimum in the range of from pH 9 to 11 (at 25° C.), temperature optimum in the range of from 40° to 50° C. (at pH 9.5), and immunochemical properties identical or partially identical to those of a protease derived from Bacillus sp. JP 395, NCIMB No. 40337. in a more specific aspect, the protease is obtainable from a strain of Bacillus sp. JP 395. In a yet more specific aspect, the protease is obtainable from Bacillus sp. JP 395, NCIMB No. 40337, or a mutant or a variant thereof.

In another aspect, the invention provides an isolated biologically pure culture of a strain of Bacillus sp. JP 395. In a more specific aspect, a strain of Bacillus sp. JP 395, NCIMB No. 40337, or a mutant or a variant thereof, is provided.

In a third aspect, the invention provides a process for the preparation of the protease, which process comprises cultivation of a protease producing strain of Bacillus sp. JP 395 in a suitable nutrient medium, containing carbon and nitrogen sources and inorganic salts, followed by recovery of the desired enzyme. In a more specific aspect, Bacillus sp. JP 395, NCIMB No. 40337, or a mutant or a variant thereof, is cultivated.

In a fourth aspect, the use of the enzyme as detergent enzyme is claimed. In a more specific aspect, the invention provides a detergent composition and a detergent additive comprising the protease.

BRIEF DESCRIPTION OF DRAWINGS

The present invention is further illustrated by reference to the accompanying drawings, in which.

DETAILED DISCLOSURE OF THE INVENTION

The microorganism

Figure 1:
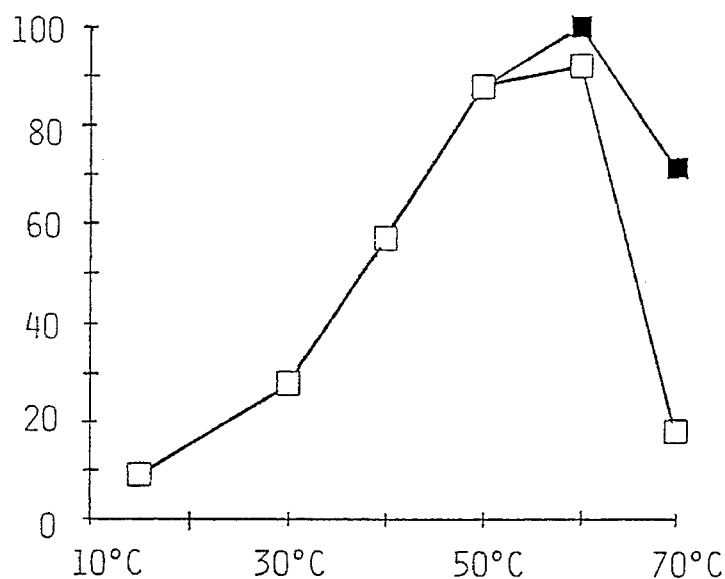
FIG. 1 shows the relation between temperature and the proteolytic activity of an enzyme according to the invention (the enzyme preparation obtained according to Ex. 1). Both curves were obtained with casein as the substrate at pH 9.5. However, the bottom curve was obtained in the presence of 0.1% STTP (sodium tripolyphosphate).

The novel microorganisms of the invention, able to produce an enzyme of the invention, were isolated essentially by the method for selection of alkalophilic Bacilli described in British Patent No. 1,243,784. One such culture, Bacillus sp. JP 395, has been deposited according to the Budapest Treaty at NCIMB, with No. 40337.

The microorganism of this invention is an aerobic, spore forming bacterium belonging to the genus Bacillus. Morphologically it can be described as motile rods with a diameter of 0.6–0.8 micron, and a length of 2–3 micron. The spores are round to ellipsoid, not swelling the sporangium, central to subterminal. Optimal temperature for growth is within 35°–40° C., and optimal pH for growth is within 8.5–10, no growth below pH 8. The microorganism forms pale yellowish colonies on nutrient agar slants, and no diffusion of pigment into the agar is observed.

Cultivation of the microorganism

The microorganism of the invention can be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes involving the cultivation of bacteria. Illustrative examples are soybean meal, cotton seed meal, peanut meal, casein, corn, corn steep liquor, yeast extract, urea and albumin. In addition, the nutrient medium should also contain usual trace substances.

Since the novel Bacillus species of this invention are alkalophilic and unable to grow at pH below 8, the cultivation is preferably conducted at alkaline pH values, which can be obtained by addition of suitable buffers such as sodium carbonate or mixtures of sodium carbonate and sodium bicarbonate, after sterilization of the growth medium. For cultivation in tank fermentors it is necessary to use artificial aeration. The rate of aeration is similar to that used in conventional tank fermentation.

After fermentation, liquid enzyme concentrates may be produced by removal of coarse material from the broth or, if desired, concentration of the broth by evaporation at low temperature or by reverse osmosis. Finally, preservatives may be added to the concentrate.

Solid enzyme preparations may be prepared from the purified and/or concentrated broth by precipitation with salts, such as $Na_2SO_4$ or water-miscible solvents, such as ethanol or acetone, removal of the water in the broth by suitable drying methods such as spray-drying may also be employed.

Assay for proteolytic activity

The proteolytic activity is determined with casein as substrate. One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5. A folder AF 228/1, describing the analytical method, is available upon request to Novo Nordisk A/S, Denmark, which folder is hereby included by reference.

The enzyme

The enzyme of the invention is a novel detergent protease. It is an alkaline protease, obtainable by cultivation of a microorganism of the invention, preferably Bacillus sp. JP 395, NCIMB No. 40337, or a mutant or a variant thereof, in a suitable nutrient medium, containing carbon and nitrogen sources and inorganic salts. The enzyme can also be obtained by recombinant DNA-technology.

The protease of the invention can be described by the following characteristics.

Physical-chemical properties

A molecular weight of 30 kD, determined by SDS-PAGE. A pI above 9.5 determined by isoelectric focusing on LKB Ampholine® PAG plates. The protease activity is inhibited by PMSF, and Turkey-egg-white proteinase inhibitor. EDTA and soybean-protein inhibitor do not influence the protease activity.

The temperature activity relationship was determined with casein as substrate. The assay for proteolytic activity described previously was used with the modification that the incubation temperature was varied in the interval of from 15° to 70° C. The result is shown in FIG. 1. The enzyme possesses proteolytic activity from temperatures below 15° C. to above 70° C., and a temperature optimum within the range of 50° to 65° C., around 60° C.

Figure 2:
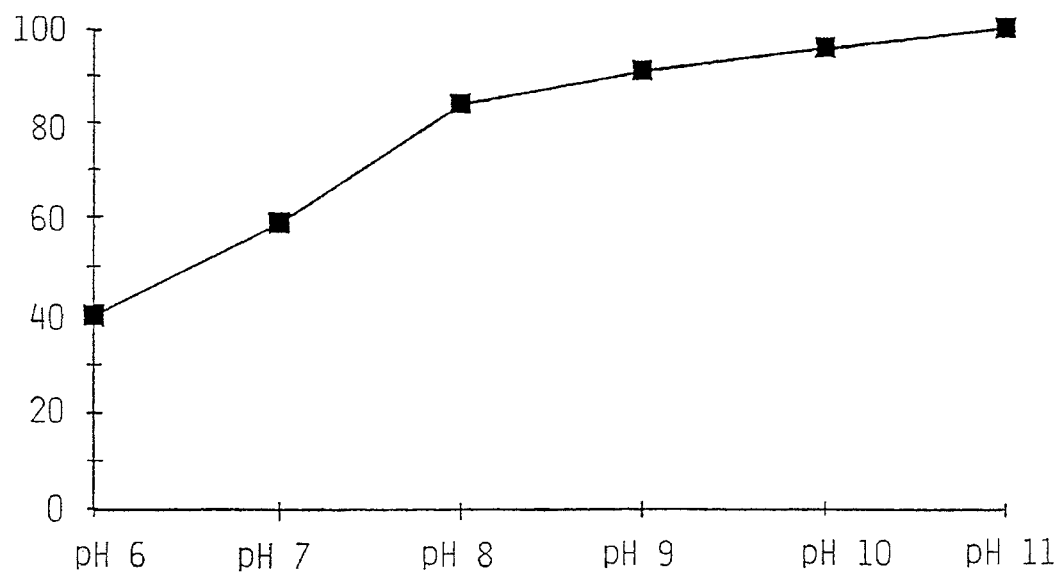
FIG. 2 shows the relation between pH and the proteolytic activity of an enzyme according to the invention (the enzyme preparation obtained according to Ex. 1, with casein as substrate and at 25° C.).

The dependence of activity on pH was determined by the same procedure, using buffers adjusted to predetermined pH values in the pH range of from 6 to 11. The result is shown in FIG. 2. The enzyme possesses proteolytic activity at pH values below 6 to above 11, with a pH optimum around pH 11 and above 90% activity in the range of pH 9 to 11.

The protease of the invention is stable for 60 minutes at 40° C. and under washing conditions, both with and without bleaches such as perborate and NOBS, in European and American type detergents.

Immunochemical properties

The immunochemical properties can be determined immunologically by cross-reaction identity tests. The identity tests can be performed by the well-known Ouchterlony double immunodiffusion procedure or by tandem crossed immunoelectrophoresis according to Axelsen, N.H.; Handbook of immunoprecipitation-in-Gel Techniques; Blackwell Scientific Publications (1983), chapters 5 and 14. The terms "antigenic identity" and "partial antigenic identity" are described in the same book, chapters 5, 19 and 20.

Monospecific antiserum was generated according to the above mentioned method by immunizing rabbits with the purified protease of the invention. The immunogen was mixed with Freund's adjuvant and injected subcutaneously into rabbits every second week. Antiserum was obtained after a total immunization period of 8 weeks, and immunoglobulin was prepared therefrom as described by N. H. Axelsen, supra.

Ouchterlony double immunodiffusion tests showed no cross reaction between the protease of the invention and the known alkaline serine proteases ALCALASE™, SAVINASE™, ESPERASE™, subtilisin BPN' and KAZUSASE™.

Detergent compositions

The detergent composition of the invention may comprise one or more surfactants, which may be of an anionic, non-ionic, cat-ionic, amphoteric or zwitterionic type, or a mixture of these. Typical examples of anionic surfactants are linear alkyl benzene sulfonates (LAS), alkyl sulfates (AS), alpha olefin sulfonates (AOS), alcohol ethoxy sulfates (AES) and alkali metal salts of natural fatty acids. Examples of non-ionic surfactants are alkyl polyethylene glycol ethers, nonylphenol polyethylene glycol ethers, fatty acids esters of sucrose and glucose, and esters of polyethoxylated alkyl glucoside.

The detergent composition of the invention may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, to optical brighteners, foam boosters, chelating agents, fillers, fabric softeners, etc. The detergent composition of the invention may be formulated substantially as described in J. Falbe [Falbe, J.; Surfactants in Consumer Products. Theory, Technology and Application; Springer Verlag 1987, vide in particular the section entitled "Frame formulations for liquid/powder heavy-duty detergents"].

It is at present contemplated that the detergent composition of the invention may contain the enzyme preparation in an amount corresponding to 0.0005–0.5 CPU of the proteolytic enzyme per liter of washing liquor.

The detergent compositions of the invention can be formulated in any convenient form, such as powders, liquids, etc.

The detergent composition of the invention may advantageously include one or more other enzymes, e.g. lipases, amylases, cellulases, oxidases, and/or peroxidases, conventionally included in detergent compositions.

The protease of the invention may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced e.g. according to GB Patent Publication No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol, a sugar or sugar alcohol, lactic acid or boric acid, according to established methods. Other enzyme stabilizers are well known in the art. Protected enzymes may be prepared according to the method disclosed in EP Patent Publication No. 238,216.

In useful embodiments, the protease of the invention may be incorporated in detergent formulations according to e.g. EP Patent Publication Nos. 342,177; 368,575; 378,261; and 378,262.

The invention is further illustrated in the following examples, which are not intended to be in any way limiting to the scope of the invention as claimed.

EXAMPLE 1

Cultivation Example

Bacillus sp. JP 395 was cultivated at 30° C. on a rotary shaking table (240 r.p.m.) in 500 ml baffled Erlenmeyer flasks containing 100 ml of medium of the following composition (per liter):

| | |
|---|---|
| Potato starch | 100 g |
| Soybean flour | 50 g |
| $Na_2HPO_4 \times 12H_2O$ | 10 g |
| Pluronic ® | 0.1 g |

The starch in the medium is liquified with α-amylase and the medium is sterilized by heating at 120° C. for 45 minutes.

After sterilization the pH of the medium is adjusted to 11.5 by addition of 10 ml of a 5M solution of sodium carbonate ($NarCO_3$).

After 5 days of incubation the proteolytic activity of the culture was determined using the method described above.

After separation of the solid material the protease was purificated by a conventional chromatographic method.

Yield from 800 ml of culture broth was 50 ml with 50 CPU/l. Purity was more than 90% as judged by SDS-PAGE.

The characteristics of the preparation prepared in accordance with this Example have been referred to earlier in this specification, and reference is made hereto.

EXAMPLE 2

Wash performance

The wash performance tests were accomplished on grass soiling on cotton, in a model miniwash system at 20° C., isothermically for 10 minutes.

2.0 g/l of a commercial American type liquid detergent were used in the test. The detergent did not contain any enzymes prior to the addition of the protease of the invention. The detergent was dissolved in approx. 6° dH (German Hardness) is water, and the pH was measured to approx. 8. The textile/wash liquor ratio was approximately 6 g textile per liter of detergent solution. The enzyme preparation according to Example 1 was used at enzyme concentrations of 0.001; 0.01 and 0.1 CPU/l.

Subsequent to washing, the fabric was rinsed in running tap water for 25 minutes and air-dried. The protease performance was determined by the change (ΔR) of the remission (%R) at 460 nm measured on a Datacolor Elrephometer 2000, ΔR being the remission after wash with protease added minus the remission after wash with no protease added.

The test results are shown in Table 1.

TABLE 1

| Enzyme Concentration; | delta R |
|---|---|
| 0.001 CPU/l | 3.1 |
| 0.01 CPU/l | 10.3 |
| 0.1 CPU/l | 16.1 |

The differential remission values show that the protease of the invention possesses good washability.

We claim:

1. An isolated protease obtained from Bacillus sp. IP 395 which has:
   (a) an apparent molecular weight of 30 kD, as determined by SDS-PAGE;
   (b) a pH optimum in the range of from pH 9 to 11 at 25° C.;
   (c) a temperature optimum in the range of from 50° to 65° C. at pH 9.5; and
   (d) an isoelectric point of above 9.5.

2. The isolated protease according to claim 1 which is active for 60 minutes at 40° C.

3. The isolated protease according to claim 1 which is active over the pH range of 6–11.

4. The isolated protease according to claim 1 which is active over the temperature range of 15°–70° C.

5. The isolated protease according to claim 1 which is inhibited by phenylmethylsulfonylfluoride.

6. The isolated protease according to claim 1 which is not inhibited by EDTA or soybean-protein inhibitor.

7. A process for the preparation of said protease according to claim 1, comprising cultivating a protease producing strain of Bacillus sp. JP 395 in a suitable nutrient medium containing carbon and nitrogen sources and inorganic salts, and recovering said protease.

8. A detergent composition comprising said protease according to claim 1 and a surfactant.

9. The detergent composition according to claim 8, further comprising one or more other enzymes selected from the group consisting of amylases, lipases, cellulases, oxidases, and peroxidases.

10. A detergent additive comprising said protease according to claim 1 in the form of a non-dusting granulate, a liquid, or a slurry.

* * * * *